United States Patent [19]
Mizuno et al.

[11] Patent Number: 4,976,356
[45] Date of Patent: Dec. 11, 1990

[54] METHOD OF AND APPARATUS FOR OPTICALLY CHECKING THE APPEARANCES OF CHIP-TYPE COMPONENTS AND SORTING THE CHIP-TYPE COMPONENTS

[75] Inventors: Touru Mizuno; Yasuhiko Kitajima, both of Tokyo, Japan

[73] Assignee: TDK Corporation, Tokyo, Japan

[21] Appl. No.: 316,791

[22] Filed: Feb. 28, 1989

[30] Foreign Application Priority Data

Mar. 31, 1988 [JP] Japan ................................. 63-79578

[51] Int. Cl.$^5$ .......................... B07C 5/02; B07C 5/342
[52] U.S. Cl. ..................................... 209/539; 198/493;
198/345.1; 209/587; 209/655; 209/906;
209/911; 209/934; 209/939; 358/106; 406/86
[58] Field of Search ............... 209/539, 551, 552, 573,
209/576, 587, 655, 939, 934, 906, 911; 358/106,
101; 324/158 F; 382/1, 8, 36; 250/223 R;
198/345, 463.6, 493, 367, 359; 406/86, 88, 89

[56] References Cited

U.S. PATENT DOCUMENTS

| | | | |
|---|---|---|---|
| 2,824,484 | 2/1958 | Thompson | 198/463.6 X |
| 2,989,179 | 6/1961 | Woods et al. | 209/657 |
| 3,198,515 | 8/1965 | Pitney | 406/86 X |
| 3,265,208 | 8/1966 | Reniker et al. | 209/655 X |
| 4,185,941 | 1/1980 | Molins | 198/493 X |
| 4,196,811 | 4/1980 | Pilesi et al. | 209/939 X |
| 4,635,111 | 1/1987 | Moore | 358/106 |
| 4,665,317 | 5/1987 | Ferriere et al. | 358/106 X |
| 4,733,459 | 3/1988 | Tateno | 198/463.6 X |
| 4,735,323 | 4/1988 | Okada et al. | 209/587 X |
| 4,845,764 | 7/1989 | Ueda et al. | 382/8 |
| 4,872,052 | 10/1989 | Liudzius et al. | 358/106 |

FOREIGN PATENT DOCUMENTS

| | | | |
|---|---|---|---|
| 77765 | 6/1981 | Japan | 324/158 F |
| 228362 | 10/1986 | Japan | 324/158 F |

Primary Examiner—Donald T. Hajec
Attorney, Agent, or Firm—Halfgott & Karas

[57] ABSTRACT

A method of optically checking the appearances of chips and sorting the chips comprises the steps of feeding chips onto chip-passage body to cause the chips to run on the chip-passage body in a predetermined direction; during the running of the chips on the chip-passage body, individually separating the chips to stop the chips one by one at each of two predetermined checking positions; irradiating light obliquely and straightly with respect to a chip at one of the predetermined checking positions to pick up an optical image of one of undersurface and top surface sides of the chip as a video signal by means of a first TV camera; irradiating light obliquely and straightly with respect to the chip at the other of the predetermined checking positions to pick up an optical image of the other of the undersurface and top surface sides of the chip as a video signal by means of a second TV camera; sending the video signals to image processing sections, each of which includes at least an analog-to-digital conversion unit, a video memory and a central processing unit, to process the video signals in the image processing sections and obtain data on the appearance of the chip and a tilt angle of the chip on each of the predetermined checking positions of the chip-passage body, thereby checking on the basis of the data whether the chip is acceptable or defective in its appearance; and thereafter sorting chips on the basis of the check results. Also, an apparatus for optically checking the appearances of chips and sorting the chips is disclosed.

28 Claims, 11 Drawing Sheets

FIG. 1
PRIOR ART
(a)
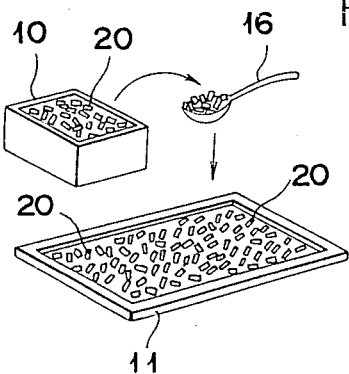
(b)
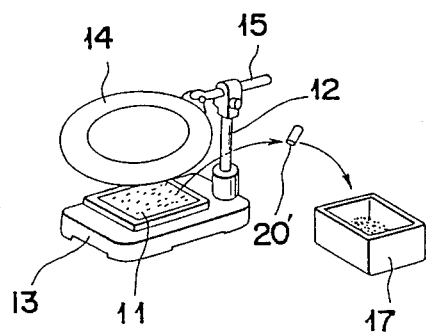
(c)
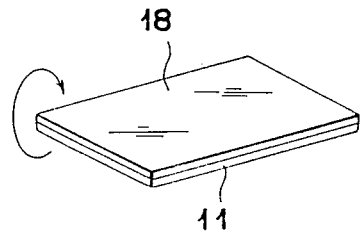

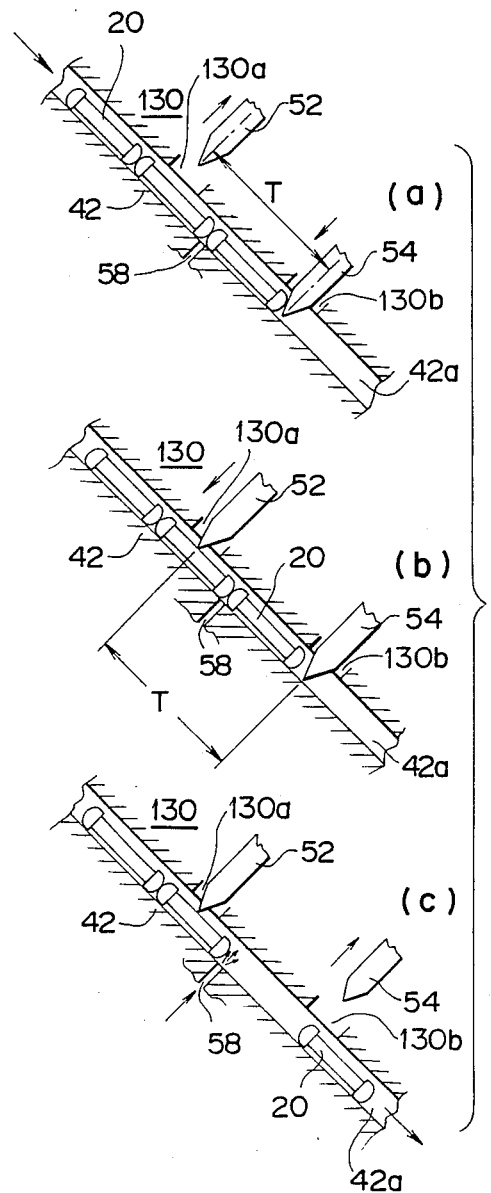

METHOD OF AND APPARATUS FOR OPTICALLY CHECKING THE APPEARANCES OF CHIP-TYPE COMPONENTS AND SORTING THE CHIP-TYPE COMPONENTS

BACKGROUND OF THE INVENTION

1. Field of the Invention

This invention relates to a method and apparatus for optically checking the appearances of chip-type electric or electronic components (e.g., chip-type capacitors, core components such as coils and the like, LC multiple components, and the like) and carrying out sorting of the chip-type components.

If a component of this type has any imperfection or defect in its exterior, for example, an unusual shape, dimensional errors, breakage, cracks and the like, such defect may badly affect the characteristics of the component and may bring about any trouble in the mounting of the component on a substrate. Therefore, it is necessary to check the appearances of components as well as the characteristics of the components.

2. Description of the Prior Art

Previously, the appearances of chip-type components were visually inspected by the naked eye or using a magnifying lens or the like.

Referring now to FIGS. 1(a) to 1(c), one of conventional methods of checking the appearances of chip-type components will be described in order to facilitate understanding of the present invention.

In FIG. 1(a), a reference numeral 10 designates a chip storage box in which a plurality of chip-type components 20 are received, and a reference numeral 11 designates a first glass pallet. In FIG. 1(b), a reference numeral 12 designates a stanchion extending upward from a base 13 and a reference numeral 14 designates a magnifying lens held by a horizontal supporting bar 15 which is supported to an upper end portion of the stanchion 12. First, chip-type components 20 are taken out of the storage box 10 by a spoon 16 to be placed on the first glass pallet 11 in a manner not to overlap one another as shown in FIG. 1(a). Secondly, the first glass pallet 11 having the chip-type components 20 put thereon is placed on the base 13. Then, a top surface side of each of the chip-type components 20 put on the first glass pallet 11 is subjected to visual inspection while each of the chip-type components 20 is magnified by the magnifying lens 14. When chip-type components having any defects in their exteriors are found through the visual inspection, the defective components 20' are picked up an collected in a waste box 17 as shown in FIG. 1(b). After the defective components 20' are all removed from the first glass pallet 11, a second glass pallet 18 is superposed on the first glass pallet 11. Then, the superposition of the first and second glass pallets 11, 18 is reversed as shown in FIG. 1(c), whereby the remaining chip-type components which were till now on the first pallet 11 shift to the second glass pallet 18 with the undersurface sides of the chip-type components facing upward. The first glass pallet 11 is removed from the second glass pallet 18 and the second glass pallet 18 is placed on the base 13. Then, the above-described procedure is substantially repeated to visually check the undersurface sides of the chip-type components on the second glass pallet 18. Thus, acceptable chip-type components are classified and sorted out from defective chip-type components.

With this conventional method, since the appearances of chip-type components are visually inspected through the magnifying lens by an inspector as described above, the checking operation typically depends on the individual inspector, so that it is impossible to set a uniform criterion for inspecting the appearances of chip-type components. In other words, criteria for inspecting the appearances of chip-type components generally vary from one field inspector to another field inspector. Therefore, chip-type components appreciated as acceptable components through the visual inspection of field inspectors may differ from one another in quality. In addition, in the conventional method, the placing of chip-type components on the first glass pallet, classifying of defective components from acceptable components, and the like are all manually carried out, so that a checking accuracy may be decreased due to an inspector fatigue, a human-caused mistake and an inspector's mood of the moment. In order to increase the checking accuracy, it is necessary to increase the number of inspectors who take charge of the checking of chip-type components. This makes chip-type components too expensive.

SUMMARY OF THE INVENTION

The present invention has been made to overcome the foregoing disadvantages of the prior art.

Accordingly, it is an object of the present invention to provide a method and apparatus for optically checking appearances of chip-type components and sorting the chip-type components, which are capable of automatically checking the appearances of chip-type components with high accuracy and at high speed.

It is another object of the present invention to provide such a method and apparatus which is capable of automatically and efficiently carrying out the classification of chip-type components after the chip-type components are subjected to the checking treatment.

It is still another object of the present invention to provide such a method and apparatus which is capable of allowing chip-type components to be smoothly transferred one by one to predetermined chip checking positions.

It is yet another object of this invention to provide such a method and apparatus which is capable of allowing chip-type components to be stopped one by one at the chip checking positions.

In accordance with one aspect of the present invention, a method of optically checking chip-type components and sorting the chip-type components is provided, which comprises the steps of feeding chip-type components onto chip-passage means to cause the chip-type components to run on the chip-passage means in a predetermined direction; during the running of the chip-type components on the chip-passage means, individually separating the chip-type components to stop the chip-type components one by one at each of two predetermined checking positions; irradiating straight and oblique light rays onto a chip-type component at one of the predetermined checking positions to pick up an optical image of one of undersurface and top surface sides of the chip-type component as a video signal by means of a first TV camera; irradiating straight and oblique light rays onto the chip-type component at the other of the predetermined checking positions to pick up an optical image of the other of the undersurface and top surface sides of the chip-type component as a video signal by means of a second TV camera; sending the video signals to image processing sections, each of which includes at least an analog-to-digital conversion unit, a video memory and a central processing unit, to process the video signals in the image processing sections to obtain data on the appearance of the chip-type component and a tilt angle of the chip-type component on each the predetermined position of the chip-passage means, thereby checking on the basis of the data whether the chip is acceptable or defective in its appearance; and sorting out the chip-type components, which have been checked in the manner described above, based on the check results.

According to a further aspect of the present invention, there is provided an apparatus for optically checking chip-type components and sorting the chip-type components. The apparatus for checking and sorting out chip-type components comprises a body; chip-passage means mounted on the body and including an elongate chip-passage body which is substantially U-shape in a vertical section, the elongate chip-passage body being formed at its two checking positions, at which the chip-type components are to be checked, of transparent material; a parts feeder mounted on said body, connected to one end of the elongate chip-passage body for feeding chip-type components onto the chip-passage body; a plurality of means for causing the chip-type components from the parts feeder to smoothly run along a U-shaped groove of the chip-passage body in a predetermined direction, and located at predetermined positions of the chip-passage body; a separating mechanism for stopping the chip-type components from the parts feeder to separate the chip-type components one by one and arranged on the body in a manner to be located near a portion of the chip-passage body; a first checking mechanism mounted on the body and adapted for optically checking, at one of the checking positions, one of undersurface and top surface sides of a chip-type component separated by the separating mechanism, and comprising a first optical system and a first image processing section including at least an analog-to-digital conversion unit, a video memory and a central processing unit, the first optical system including first lighting means for straightly and obliquely irradiating light toward the chip-type component and a first TV camera for picking up, as a video signal, an image of the one of the undersurface and top surface sides of the chip-type component to which light rays from the first lighting means are obliquely and straightly irradiated, the first TV camera being electrically connected to the analog-to-digital conversion unit of the first image processing section; a second checking mechanism mounted on the body in a manner to be located next to the first checking mechanism and for optically checking, at the other of the checking positions, an image of the other of the undersurface and top surface sides of the chip, and comprising a second optical system and a second image processing section including at least an analog-to-digital conversion unit, a video memory and a central processing unit, the second optical system including second lighting means for straightly and obliquely irradiating light toward the chip-type component and a second TV camera for picking up, as a video signal, an image of the other of the undersurface and top surface sides of the chip-type component to which light rays from the second lighting means are obliquely and straightly irradiated, the second TV camera being electrically connected to the analog-to-digital conversion unit of the second image processing section; and a sorting mechanism arranged at the other end of the chip-passage body for receiving the chip-type components from the chip-passage body to sort the chip-type components on the basis of check data obtained by the first and second checking mechanisms.

BRIEF DESCRIPTION OF THE DRAWINGS

These and other objects and many of the attendant advantages of the present invention will be readily appreciated as the same becomes better understood by reference to the following detailed description when considered in connection with the accompanying drawings, in which like reference numerals designate like or corresponding parts throughout; wherein:

FIGS. 1(a) to 1(c) are each a schematic perspective view of assistance in explaining a conventional method of checking and sorting chip-type components;

FIGS. 6(a) to 6(c) are each a schematic fragmentary sectional side elevation view of a second cover plate and a portion of the chip-passage body on which the second cover plate is arranged, taken along a longitudinal direction of a groove of the chip-passage body, and of assistance in explaining a manner of operation of pins of a chip separating mechanism;

FIG. 10 is a schematic enlarged fragmentary plan view showing a shutter device of the first chip checking mechanism or of the second checking mechanism;

FIG. 11 is a block view showing image processing sections of the first and second checking mechanisms;

DETAILED DESCRIPTION OF THE PREFERRED EMBODIMENT

Now, an apparatus on which a method of optically checking the appearances of chip-type components and sorting the chip-type components according to the present invention may be performed will be described hereinafter with reference to the accompanying drawings.

Figure 2:
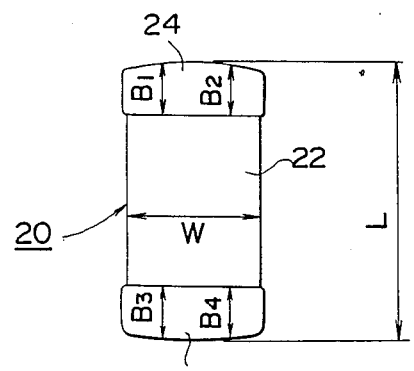
FIG. 2 is a schematic enlarged front view showing an example of a chip-type component which is to be handled by an apparatus for performing a method of checking and sorting chip-type components according to an embodiment of this invention.

As an example of a chip-type component to be checked by a checking and sorting apparatus according to the present invention, a chip-type capacitor will be referred to in the following. Referring to FIG. 2, a chip-type capacitor 20 (hereinafter referred to as "chip") comprises a body 22 and two electrodes 24 mounted at two ends of the body 22. In an embodiment of the present invention which will be described below, items to be checked includes the total length dimension of the chip 20 which is generally denoted by a designator L, the width dimension of the body 22 which is generally denoted by a designator W, the width dimensions of the electrodes 24 which are generally denoted by designators B1, B2, B3 and B4, breakage of the chip and the like.

Figure 3:
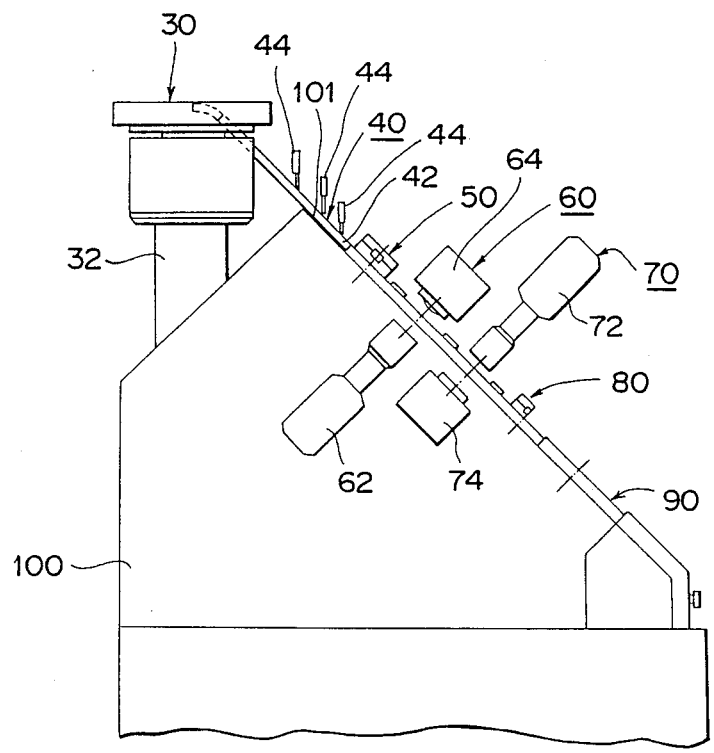
FIG. 3 is a schematic side view showing the checking and sorting apparatus according to the embodiment of this invention.
Figure 4:
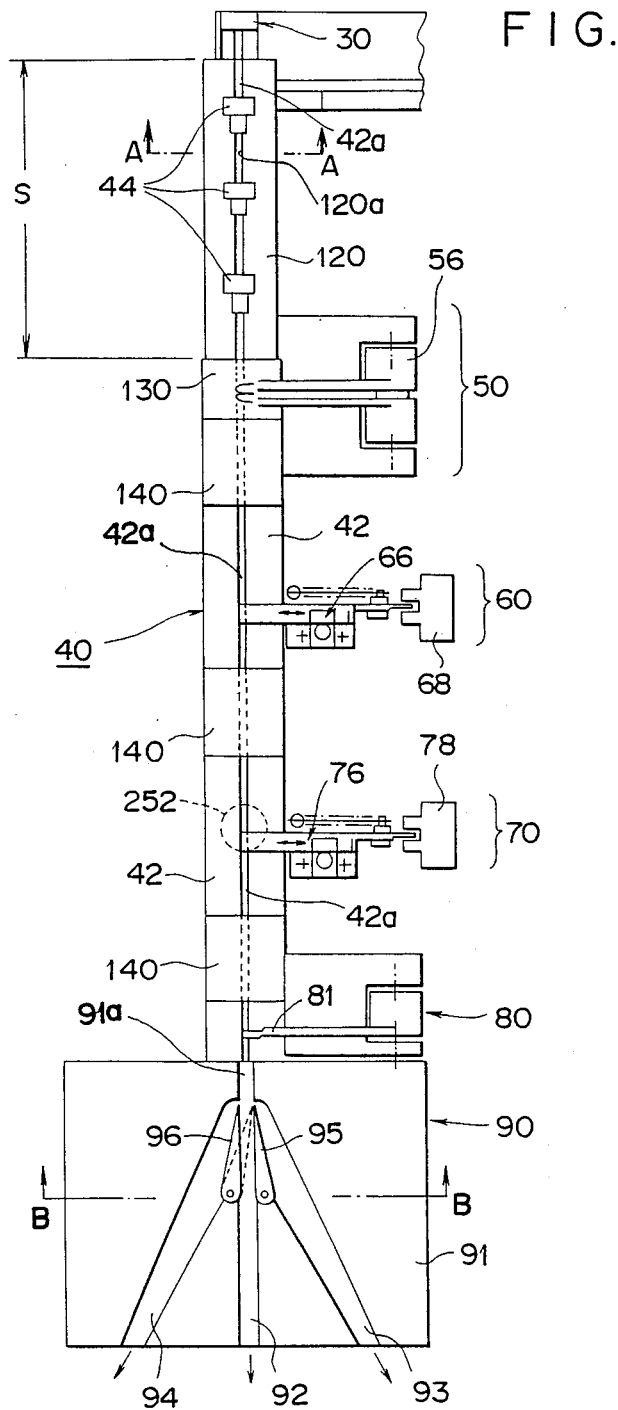
FIG. 4 is a schematic plan view of the apparatus shown in FIG. 3, wherein fourth and fifth cover plates are removed from portions of a chip-passage body and a sixth cover plate is removed from a base of a chip sorting mechanism for clarity of illustration.

Referring now to FIGS. 3 and 4, there is illustrated an apparatus for checking the appearances of chips and sorting the chips according to an embodiment of this invention. The checking and sorting apparatus according to the embodiment of the present invention generally includes a body 100 having a top inclined plane 101; a parts feeder 30 for feeding chips and supported by a stanchion 32, which extends upward from the body 100, in a manner to be located in the proximity of an upper end of the inclined plane 101 of the body 100; chip-passage means 40 comprising an elongate chip-passage body 42 of a substantially U-shape in vertical section which is provided on the inclined plane 101 of the body 100 in a manner to extend in a downward direction of the body 100 and further extends upward to be connected at its upper end to the parts feeder 30; a chip separating mechanism 50 for individually separating the chips fed from the parts feeder 30; a first checking mechanism 60 for checking an undersurface side of each of the chips; a second checking mechanism 70 for checking a top surface side of each of the chips; a counting mechanism 80 for counting the number of the chips traveling on the chip-passage body 100; and a chip sorting mechanism 90 for sorting the chips. The chip separating mechanism 50, the first checking mechanism 60, the second checking mechanism 70 and the counting mechanism 80 in turn are arranged along the elongate chip-passage body 42 of the chip-passage means 40 in the downward direction. The chip sorting mechanism 90 is arranged at a lower end of the chip-passage body 42.

In the illustrated embodiment, the parts feeder 30 takes the form of a vibratory bowl feeder. The upper end of the chip passage body 42 is connected to a chip outlet of the vibratory bowl feeder through which chips from the vibratory bowl feeder are adapted to pass to ride on the chip-passage body 42. The vibratory bowl feeder is well known in the arts and will not be described.

In the illustrated embodiment, the inclined plane 101 of the body 100 is slant at angle of about 45° with respect to the horizontal plane, so that the U-shaped chip-passage body 42 on the inclined plane 101 is also inclined at an angle of about 45° with respect to the horizontal plane. Since the U-shaped chip-passage body 42 is inclined as described above, chips fed from the parts feeder 30 will slip down on the chip-passage body 42 along a groove 42a of the chip-passage body 42. However, there is a possibility that a static electricity and a frictional resistance may be produced between the chips and the chip-passage body 42 while the chips slip down on the chip-passage body 42, whereby the chips will be prevented from smoothly slipping down on the chip-passage body 42. In order to avoid such trouble, the illustrated embodiment further comprises means for facilitating the slipping-down of chips as will be described later.

Figure 5:
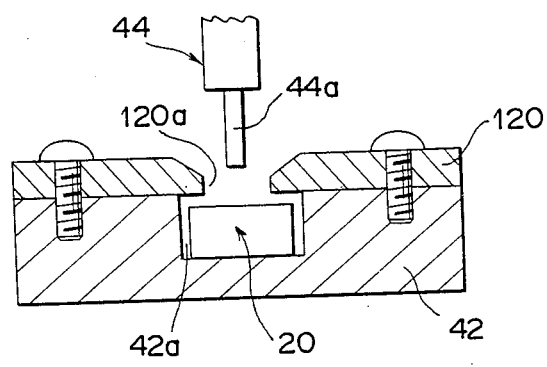
FIG. 5 is a schematic enlarged vertical sectional view of a first cover plate and a portion of the chip-passage body on which the first cover plate is arranged, taken on a plane indicated at FIG. 4 by a line A-A.

The apparatus according to the embodiment further comprises a plurality of air jetting heads 44 for facilitating the slipping-down of chips on the chip-passage body 42. Referring to FIG. 5, each of the air jetting heads 44 includes an air jet nozzle 44a which is connected to any suitable air-supplying means (not shown) and from which air jet nozzle 44a air is adapted to jet. More particularly, a first elongate cover plate 120 having an elongate through-hole 120a extending along its longitudinal direction is located on an area S (see FIG. 4) of the chip-passage body 42 between the parts feeder 30 and the chip separating mechanism 50, above which first cover plate 120 the air jetting heads 44 (only one is shown in FIG. 5) are located in a manner to be arranged at equal intervals along the longitudinal direction of the cover plate 120. Also, each of the air jetting heads 44 is obliquely arranged in such a manner that a tip end of its air jet nozzle 44a directs toward the through-hole 120a of the cover plate 120 and in a downward direction of the cover plate 120. Thus, air jetting from each of the air jet nozzles 44a passes through the through-hole 120a of the first cover plate 120 to flow into the groove 42a of the U-shaped chip-passage body 42, whereby chips fed from the parts feeder 30 can be smoothly transferred downward on the chip-passage body 42 along the groove 42a of the chip-passage body 42.

The chip separating mechanism 50 briefly described above is located at a position lower than the arranging positions of the air jetting heads 44. Referring now to FIG. 6, the chip separating mechanism comprises first and second pins 52, 54 which are located above a second cover plate 130 which is arranged on a portion of the chip-passage body 42. The first and second pins 52, 54 are arranged at a distance T therebetween along the longitudinal direction of the chip-passage body 42, which distance T is set to an extent that is more than the length dimension of one chip but is less than the total length dimension of two chips. Formed at portions of the second cover plate 130 which are right below the first and second pins 52, 54 are through-holes 130a, 130b. The first and second pins 52, 54 are connected to any suitable actuating means 56 (see FIG. 4) and adapted to be moved vertically with respect to the chip-passage body 42 by the actuating means 56. When each of the first and second pins 52, 54 is moved downward by the actuating means 56, it operatively passes through the through-hole 130a (130b) of the second cover plate 130 to go at its tip end portion into the groove 42a of the chip-passage body 42. These pins 52, 54 serve as means to individually separate chips which have successively slipped down on the chip-passage body 42 along the groove 42a of the chip-passage body 42 in the manner as described above. As shown in FIG. 6(a), when chips 20 fed from the parts feeder 30 slip down on the chip-passage body 42, the first pin 52 is at an upward position, whereas the second pin 54 is at a downward position with its tip end moving into the groove 42a of the chip-passage body 42. Therefore, the foremost one of the chips 20 having slipped down on the chip-passage body 42 stops against the second pin 54, resulting in the foremost and subsequent chips staying on a portion of the chip-passage body 42. At this time, the first pin 52 is moved downward to hold the next chip against the bottom surface of the groove 42a of the chip-passage body 42 through its tip end as shown in FIG. 6(b). Then, the second pin 54 is moved upward in order to release the foremost chip therefrom as shown in FIG. 6(c). At this time, the foremost chip may be dragged to the next chip due to a static electricity which may be produced between the foremost and next chip or the foremost chip may remain at the same position on the chip-passage body 42 due to a frictional resistance which may be produced between the foremost chip and the chip-passage body 42. Therefore, even though the second pin 54 is moved upward to release the foremost chip therefrom, the foremost chip may not slip down on the chip-passage body 42. It is necessary to avoid such trouble. For this purpose, in the illustrated embodiment, means for causing the foremost chip to be smoothly transferred downward on the chip-passage body 42 is provided. More particularly, formed at a portion of a bottom wall of the groove 42a of the chip-passage body 42 which positionally corresponds to a substantially middle position between the pins 52 and 54 is an air passage 58 which extends perpendicularly to the bottom surface of the groove 42a of the chip-passage body 42 to communicate with the groove 42a of the chip-passage body 42 at its upper end. The air passage 58 is connected at its lower end to any suitable air-supplying means (not shown) which is adapted to supply air synchronously with the upward movement of the pin 54. As shown in FIG. 6(c), the air passage 58 jets air therethrough synchronously with the upward movement of the second pin 54, resulting in the foremost chip being smoothly transferred down on the chip-passage body 42 by the airflow. Thus, the foremost chip is separated from the subsequent chips. Thereafter, as shown in FIG. 6(a), the second pin 54 is moved downward while the first pin 52 is moved upward. Then, the above-described procedure is repeated to individually separate chips to transfer the chips one by one toward the first checking mechanism 60 which is located at a position lower than the arranging position of the chip separating mechanism 50. Incidentally, the first pin 52 and the second pin 54, when they are moved downward, are abutted against a chip and the bottom surface of the groove 42a of the chip-passage body 42, respectively. At this time, any shocks may be delivered to the first and second pins 52, 54, so that it is necessary to absorb such shocks. For this purpose, the first and second pins 52, 54 comprise any suitable shock-absorbing means (not shown).

Figure 7:
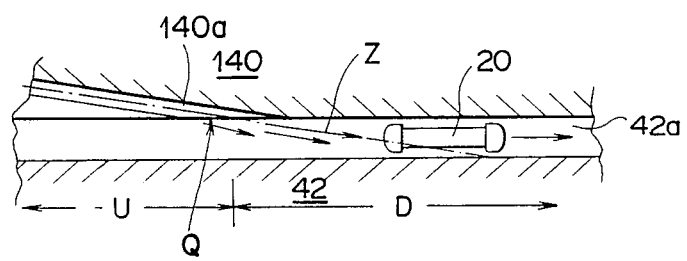
FIG. 7 is a schematic fragmentary sectional side elevation view of one of third cover plates and a portion of the chip-passage body on which the one of the third cover plates is arranged, taken along the longitudinal direction of the groove of the chip-passage body, and of assistance in explaining a manner of transferring of chip-type components along the groove of the chip-passage body by airflow.

In addition to the air passage 58, the illustrated embodiment further has an air passage, which also serves to facilitate the slipping-down of chips on the chip-passage body 42, at each of positions between the arranging position of the chip separating mechanism 50 and the arranging position of the first checking mechanism 60, between the arranging position of the first checking mechanism 60 and the arranging position of the second checking mechanism 70, and between the arranging position of the second checking mechanism 70 and the arranging position of the counting mechanism 80. More particularly, as shown in FIG. 4, a third cover plate 140 is located on each of portions of the chip-passage body 42 between the arranging position of the chip separating mechanism 50 and the arranging position of the first checking mechanism 60, between the arranging position of the first checking mechanism 60 and the arranging position of the second checking mechanism 70, and between the arranging position of the second checking mechanism 70 and the arranging position of the counting mechanism 80. Referring now to FIG. 7, each of the third cover plates 140 (only one is shown in FIG. 7) has a certain thickness. The cover plate 140 is formed with an air jet passage 140a. The air jet passage 140a is formed in the third cover plate 140 such that it obliquely extends in the thickness direction of the cover plate 140 to communicate at its lower end with the groove 42a of the chip-passage body 42 and is connected at its upper end to any suitable air-supplying means (not shown), whereby air supplied from the non-shown air-supplying means passes through the air jet passage 140a to flow into the groove 42a of the chip-passage body 42. The air jet passage 140a may be formed in the cover plate 140 such that it is inclined at an angle less than 15° with respect to the bottom surface of the groove 42a of the chip-passage body 42. In the illustrated embodiment, the air jet passage 140a is inclined at an angle of about 8° with respect to the bottom surface of the groove 42a of the chip-passage body 42. In FIG. 7, the flow of air jetted from the non-shown air-supplying means is denoted by a designator Z. The air flow Z flowing into the groove 42a of the chip-passage body 42 can create a sucking force in an area U of the groove 42a of the chip-passage body 42 which is higher than a position Q (hereinafter referred to as "communicating position") at which the air jet passage 140a communicates with the groove 42a of the chip-passage body 42, resulting in chips 20 from the parts feeder 30 being pulled down on the chip-passage body 42 in the area U of the groove 42a of the chip-passage body 42. Further, in an area D of the groove 42a of the chip-passage body 43, which is lower than the communicating position Q, the chips are pushed in the downward direction of the chip-passage body 42 by the air flow Z. Thus, the chips fed from the parts feeder 30 are transferred downward on the chip-passage body 42 in the area U of the groove 42a due to the sucking force produced by the air flow Z and, when the chips pass by the communicating position Q, they are pushed in the downward direction of the chip passage-body 42 by the air flow Y, whereby the chips can be smoothly transferred downward on the chip-passage body 42 along the groove 42a of the chip-passage body 42. Incidentally, in the illustrated embodiment, the air jet passage 140a is formed in the cover plate 140 but it may be formed in the bottom wall of the groove 42a of the chip-passage body 42.

Returning now to FIG. 3, it will be seen that the first checking mechanism 60 briefly described above is located at a position lower than the arranging position of the chip separating mechanism 50 and includes a TV camera 62 which is located below a portion of the chip-passage body 42, and lighting means 64 which is located above the portion of the chip-passage body 42 so that it is aligned with the TV camera 62. More particularly, the TV camera 62 and lighting means 64 are arranged so as to interpose the portion of the chip-passage body 42 therebetween. The second checking mechanism 70 is located at a position lower than the arranging position of the first checking mechanism 60 an also includes a TV camera 72 and lighting means 74 which are arranged in a manner to interpose a portion of the chippassage body 42 therebetween and in a manner to be aligned with each other. Contrary to the arrangement of the TV camera 62 and lighting means 64 of the first checking mechanism 60, the TV camera 72 of the second checking mechanism 70 is located above the portion of the chip-passage body 42 and the lighting means 74 of the second checking mechanism 70 is located below the portion of the chip-passage body 42.

Figure 8:
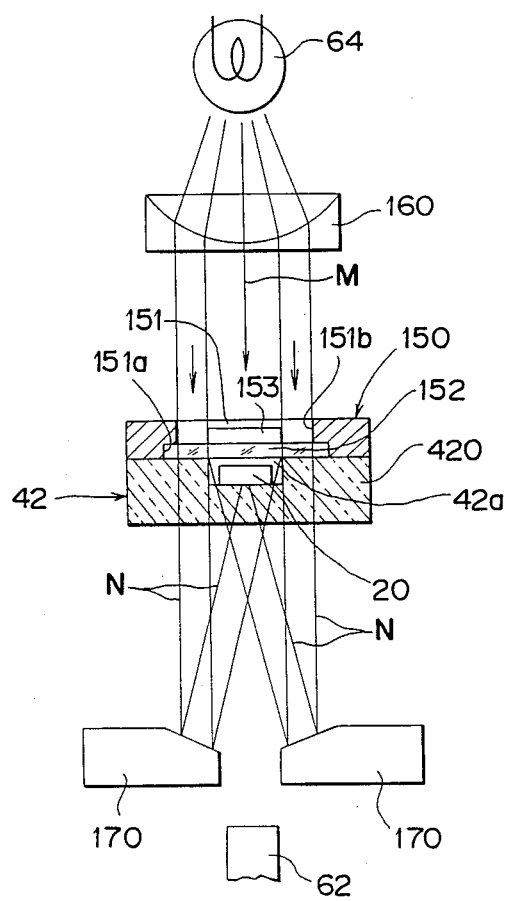
FIG. 8 is a schematic view of assistance in explaining a manner of operation of an optical system of a first chip checking mechanism.

Referring now to FIG. 8, the portion 420 of the chippassage body 42 between the TV camera 62 and lighting means 64 of the first checking mechanism 60 is made of transparent material, e.g., tempered glass or the like. Arranged on the portion 420 of the chip-passage body 42 is a fourth cover plate 150 which is made of metal. The fourth cover plate 150 is formed with a central through-hole 151 which consists of a large circular portion 151a at a bottom portion of the cover plate 150 and a small circular portion 151b at a top portion of the cove plate 150. Fitted in the large circular portion 151a of the through-hole 151 of the cover plate 150 is a circular plate 152 which is made of transparent material, e.g., tempered glass or the like, on a top surface of which transparent plate 152 a frosted glass plate 153 smaller than the transparent plate 152 is provided. In the illustrated embodiment, a condenser lens 160 is arranged between the lighting means 64 and the cover plate 150, and a pair of reflectors 170 are arranged between the TV camera 62 and the portion 420 of the chip-passage body 42. Light from the lighting means 64 is adapted to be condensed in a manner as shown in FIG. 8 by means of the condenser lens 160. The so-condensed light passes through the frosted glass plate 153 and the transparent plate 152 at its substantially central area to be straightly irradiated to a chip 20, and passes through the transparent plate 152 and the transparent portion 420 of the chip-passage body 42 at its area about the central area to be obliquely reflected from the reflectors 170 toward the chip 20. Then, the TV camera 62 picks up an image of the undersurface side of the chip onto which the light rays are straightly and obliquely irradiated in the manner as described above.

Figure 9:
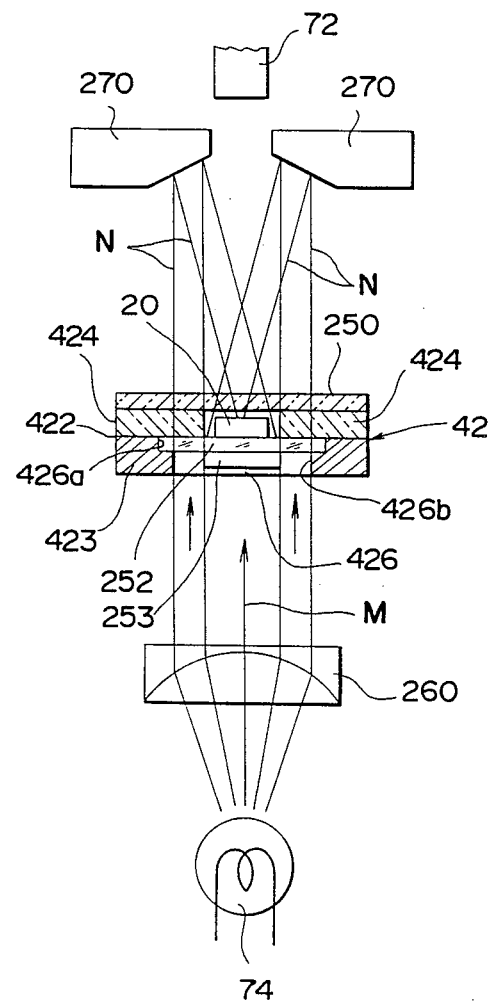
FIG. 9 is a schematic view of assistance in explaining a manner of operation of an optical system of a second chip checking mechanism.

The chip-passage body 42 has a substantially U-shape in vertical section as described above, and comprises a base and left and right side walls. Referring now to FIG. 9, there is illustrated an optical system of the second checking mechanism 70. Unlike the optical system of the first checking mechanism 60, at the portion 422 of the chip-passage body 42 between the TV camera 72 and lighting means 74 of the second checking mechanism 70, the base 423 of the portion 422 of the chip-passage body 42 is made of metal and the side walls 424 of the portion 422 of the chip-passage body 42 are made of transparent material, e.g., tempered glass or the like. Arranged on the portion 422 of the chip-passage body 42 is a fifth cover plate 250 which is made of transparent material, e.g., tempered glass or the like, unlike the fourth cover plate 150. The base 423 of the portion 422 of the chip-passage body 42 between the TV camera 72 and lighting means 74 of the second checking mechanism 70 is formed with a central through-hole 426 which consists of a large circular portion 426a at a top portion of the base 423 and a small circular portion 426b at a bottom portion of the base 423. Fitted in the large circular portion 426a of the through-hole 426 is a circular plate 252 which is made of transparent material, e.g., tempered glass or the like, on an undersurface of which transparent plate 252 a frosted glass 253 smaller than the circular plate 252 is provided. Like the optical system of the first checking mechanism 60, the optical system of the second checking mechanism 70 includes a condenser lens 260 which is arranged between the lighting means 74 and the portion 422 of the chip-passage body 42, and a pair of reflectors 270 which are arranged between the TV camera 72 and the fifth cover plate 250. Light from the lighting means 74 is adapted to be condensed in a manner as shown in FIG. 9 by means of the condenser lens 260. The so-condensed light passes through the frosted glass plate 253 and the transparent plate 252 at its substantially central area to be straightly irradiated to a chip 20, and passes through the transparent plate 252, the side walls 424 and the fifth cover plate 250 at its area about the central area to be obliquely reflected from the reflectors 270 toward the chip 20. Then, the TV camera 72 picks up an image of the top surface side of the chip 20 onto which the light rays are straightly and obliquely irradiated in the manner as described above.

Incidentally, as well known to those of ordinary skill in the art, there is high contrast in brightness between a central area and an area about the central area within light rays from a light source, namely, the central area of the light rays is brighter than the area about the central area of the light rays, resulting in differences in brightness between a portion of an article illuminated by the central area of the light rays and a portion of the article illuminated by the area about the central area of the light rays. This will make an image of the article unclear. It is necessary to prevent such trouble which may be brought about due to a light characteristic described above. For this purpose, in the illustrated embodiment, the frosted glass plate 153 (253) is arranged in paths of central portions of light rays from the lighting means 64 (74), or in paths of light rays straightly irradiated to a chip, thereby making the brightness between a portion of a chip illuminated by the straight light rays M and a portion of the chip illuminated by light rays N in an area about the straight light rays M uniform. Thus, in the illustrated embodiment, the TV camera 62 (72) can pick up a sharp image of a chip.

The first checking mechanism 60 further comprises a shutter device 66 for stopping a chip 20 on the portion 420 of the chip-passage body 42 between the TV camera 62 and the lighting means 64 as shown in FIG. 4, and a shutter confirming sensor 68. Likewise, the second checking mechanism 70 further comprises a shutter device 76 for stopping the chip 20 on the portion 422 of the chip-passage body 42 between the TV camera 72 and the lighting means 74, and a shutter confirming sensor 78. Referring now to FIG. 10, the shutter devices 66 and 76 include stopping bars 660 and 760, respectively, which are adapted to be moved in a direction perpendicular with respect to the chip-passage body 42 by any suitable actuating means (not shown) synchronously with the slipping-down of a chip on the chip-passage body 42. More particularly, one of the side walls of each of the portions 420 and 422 of the chip-passage body 42 is formed with a notch 450 which extends in a width direction of the side wall. Through the notches 450 of the portions 420, 422 of the chip-passage body 42, the stopping bars 660 and 760, when actuated by the unshown actuating means, are adapted to move in and out of the groove 42a of the chip-passage body 42. The stopping bar 660 (760) is moved in the groove 42a of the chip-passage body 42 by means of the actuating means synchronously with the slipping-down of a chip 20 on the chip-passage body 42, whereby the chip 20 slipping down on the chip-passage body 42 stops against a tip end of the stopping bar 660 (760) to stay on the portion 420 (422) of the chip-passage body 42. Then, the chip 20 staying on the portion 420 (422) of the chip-passage in the manner as described above is subjected to checking treatment as will be described later. Incidentally, each of the stopping bars 660, 770 is made of transparent material, e.g., tempered glass, or stainless steel with a specular surface finish. In the case where the stopping bar is made of transparent material, light from the lighting means 64 (74) passes through the stopping bar, resulting in the TV camera 62 (72) not picking up an image of the stopping bar. Also, in the case where the stopping bar is made of such stainless steel, light from the lighting means 64 (74) is reflected from the stopping bar. Consequently, when the TV camera 62(72) picks up an image of a chip, it also pick up the reflection from the stopping bar. However, when the image of the chip is displayed on a screen of a monitor as will be described later, an image of the stopping bar is displayed as a glistening image. From the foregoing, it will readily be understood that even though the stopping bar 660 (770) is arranged within view of the TV camera 62 (72), this will not affect the checking operation of a chip.

Referring to FIG. 11, there is illustrated image processing sections 600 and 700 of the first and second checking mechanisms 60, 70. The image processing sections 600 and 700 are electrically connected to the TV camera 62 and 72, respectively. More particularly, the image processing section 600 of the first checking mechanism 60 comprises an analog-to-digital conversion (A/D conversion) unit 601 electrically connected to the TV camera 62, a video memory 602 electrically connected to the A/D conversion unit 601, and a central processing unit (CPU) 603 for an image processing and electrically connected to the video memory 602. Likewise, the image processing section 700 of the second checking mechanism 70 comprises an analog-to-digital conversion (A/D conversion) unit 701 electrically connected to the TV camera 72, a video memory 702 electrically connected to the A/D conversion unit 701, and a central processing unit (CPU) 703 for an image processing and electrically connected to the video memory 702. Further, the CPUs 603 and 703 are electrically connected to a CPU 800 for synthetically judging checking results of the undersurface and top surface sides of a chip 20 obtained by the CPUs 603 and 703 and for sending commands to the above-described air-supplying means, the actuating means for the pins 52 and 54 of the chip separating mechanism 50, the actuating means of the shutter devices 66 and 76, the counting mechanism 80 and the chip sorting mechanism 90 in order to control the operations of these mechanisms. Furthermore, the video memories 602 and 702 are electrically connected to a cathode-ray-tube (CRT) monitor 802 through a switch 801.

Images of the undersurface and top surface sides of a chip 20 respectively picked up by the TV camera 62 and 72 are adapted to be inputted as video signals to the A/D conversion units 601 and 701, respectively. Then, the video signals are respectively digitalized in the A/D converison units 601 and 701 to be memorized in the video memories 602 and 702, and are then sent to the CPUs 603 and 703 to be processed by the CPUs 603 and 703.

Figure 12A:
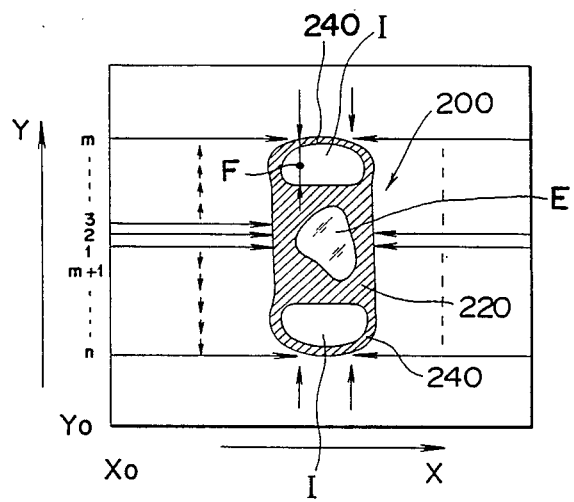
FIG. 12(a) is a schematic view of assistance in explaining a manner of sweeping an image of a chip-type component.
Figure 12B:
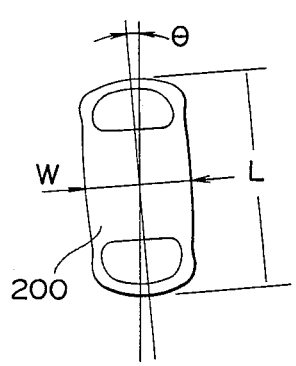
FIG. 12(b) is a schematic view of assistance in explaining an inclination of a chip-type component on the chip-passage body.

In the illustrated embodiment, an image of a chip is picked up by the TV camera and displayed on a screen of the monitor 802, in which addresses on the screen of the monitor 802 which are to be swept are selected and an area of the screen at the selected addresses is swept, whereby dimension of the chip is measured. Then, the measurements on the dimension of the chip which are obtained at the swept addresses are compared with predetermined values, thereby judging whether the chip is accceptable or defective. The monitor is designed to produce black-and-white image. Referring now to FIGS. 12(a) and 12(b), an image 220 of a body portion of a chip appears blackly on the screen of the monitor, whereas images 240 of electrode portions of the chip may appear on the screen with their central parts I whitening and parts about the parts I blackening. Also, a chip body image 220 may be displayed on the screen with its part E whitening. This may occur by the condition of a surface of the chip body. In the illustrated embodiment, an image 200 of a chip picked up by the TV camera as described above is adapted to be displayed on a substantially central portion of the screen of the monitor 802. When no image of a chip is displayed on the screen, it is determined that a chip is not on the portion 420 (422) of the chip-passage body 42 between the TV camera 62 (72) and the lighting means 64 (74). The screen is swept, at addresses corresponding to its central portion, from both sides of the screen and also up and down. At this time, boundaries at which the colors within the chip image 200 change are detected, thereby determining a contour of the chip image. Then, the total length dimension L of the chip, the width dimension W of the chip are measured and a tilt angle $\theta$ of the chip on the portion 420 (422) of the chip-passage body 42 (see FIG. 12(b)) is detected. If the chip has actually any breakages and cracks therein, such breakages and cracks are also detected. Incidentally, the groove 42a of the chip-passage body 42 has a width more than that of a chip in order to allow the chip to smoothly slip down on the chip-passage body. Therefore, when the chip reaches the portion 420 (422) of the chip-passage body 42, it may be stopped, by the stopping bar 660 (770) of the shutter device 66 (76), in a state of inclining on the portion 420 (422) of the chip-passage body 42 in a width direction of the chip-passage body 42. Such inclination of the chip will cause errors in the measurements on the dimension of the chip. Therefore, in the illustrated embodiment, the measurements on the dimension of the chip are corrected on the basis of the measurements in such tilt angle $\theta$ of the chip. The tilt angle $\theta$ of the chip is determined by deviation between a point, which is determined by minimum one of addresses of the Y-coordinate and one of addresses of the X-coordinate, which corresponds to the minimum address of the Y-coordinate, within the central portion of the screen on which the chip image 200 is displayed, and a point, which is determined by maximum one of adresses of the Y-coordinate and one of the addresses of the X-coordinate, which corresponds to the maximum address of the Y-coordinate, within the central portion of the screen. Checking of the electrodes of the chip is carried out by dividing the measured dimension W of the chip image 200 into three equal divisions on the screen with two lines and sweeping the screen along the lines dividing the measured dimension W of the chip image 200 to measure width dimensions of parts of the electrode images 240 along the lines. At this time, the measurements on the width dimensions of the parts of the electrode images along the lines are corrected on the basis of the measurements on the tilt angle $\theta$ of the chip. As described above, a chip image may be displayed on the screen with the part E of its body image whitening by a condition of a surface of the chip body. In the illustrated embodiment, data on dimensions of white and black areas of a chip image allowable to be displayed on the screen are previously memorized in order to distinguish the white electrode images 240 from the white part E of the chip body image. If dimensions of white and black areas of electrode images displayed on the screen are within the memorized data, it is determined that the chip is acceptable. Also, an electrode of a chip may has dirt, dust, a crack and/or a breakage on its surface. When an image F of such dirt or the like is displayed blackly within a white electrode image I on the screen as shown in FIG. 12(a), if the black image F is within the memorized dimensional data, such black image F may not be taken into consideration.

Thus, the checking method according to the present invention is carried out not by a simple sequential address-sweeping but by a selective address-sweeping, so that the checking of a chip according to the present invention may be carried out at high speed.

Figure 13:
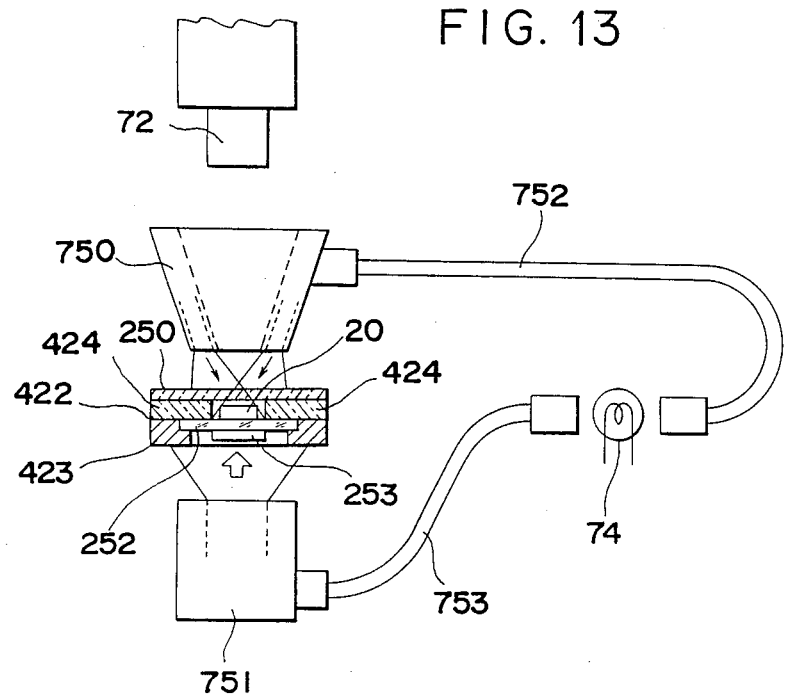
FIG. 13 is a schematic view of a modification of the optical system shown in FIG. 9.

Referring to FIG. 13, there is illustrated a modification of the optical system of the second checking mechanism 70 shown in FIG. 9. In the modification of FIG. 13, parts which are identical to those shown in FIG. 9 are identified by the same designators and the description of them will not be repeated.

The modification of FIG. 13 comprises a first light irradiating head 750 for obliquely irradiating light toward a chip 20 and arranged between the TV camera 72 and the fifth cover plate 250 arranged on the portion 422 of the chip-passage body 42, and a second light irradiating head 751 for straightly irradiating light to the chip 20 on the portion 422 of the chip-passage body 42 and located below the portion 422 of the chip-passage body 42. The first light irradiating head 750 has a substantially cone-like and ring-like body. A first fiber cable 752 is connected at one end thereof to the first light irradiating head 750. Also, a second fiber cable 753 is connected at one end thereof to the second light irradiating head 751. At a position between the other ends of the first and second fiber cables 752, 753, a light source 74 is arranged. Thus, light rays emitted from the light source 74 are supplied through the first and second fiber cables 752, 753 to the first and second light irradiating heads 750, 751. Then, the light rays are irradiated obliquely and straightly to the chip 20 on the portion 422 of the chip-passage body 42 by means of the first and second light irradiating heads 750, 751, respectively. In the modification of FIG. 13, it is possible to easily control paths of the light rays from the light source 74 and light intensity when compared to the optical system of FIG. 9. Incidentally, it should be understood that the optical system of FIG. 13 may also be employed as an optical system of the first checking mechanism 60.

After the checking of a chip is completed in the manner described above, the stopping bar 760 of the shutter device 76 of the second checking mechanism 70 having stopped the chip on the portion 422 of the chip-passage body 42 till now is actuated to move out of the groove 42a of the chip-passage body 42, resulting in the chip slipping down on the chip-passage body 42 along the groove 42a of the chip-passage body 42. During the slipping-down of the chip on the chip-passage body 42, the chip is counted by means of the counting mechanism 80 which comprises a photoelectric detector (not shown) and a stopper pin 81 (see FIG. 4) similar to the pins 52, 54 of the chip separating mechanism 50. After the chip is counted by the counting mechanism 80, it reaches the chip sorting mechanism 90.

Figure 14:
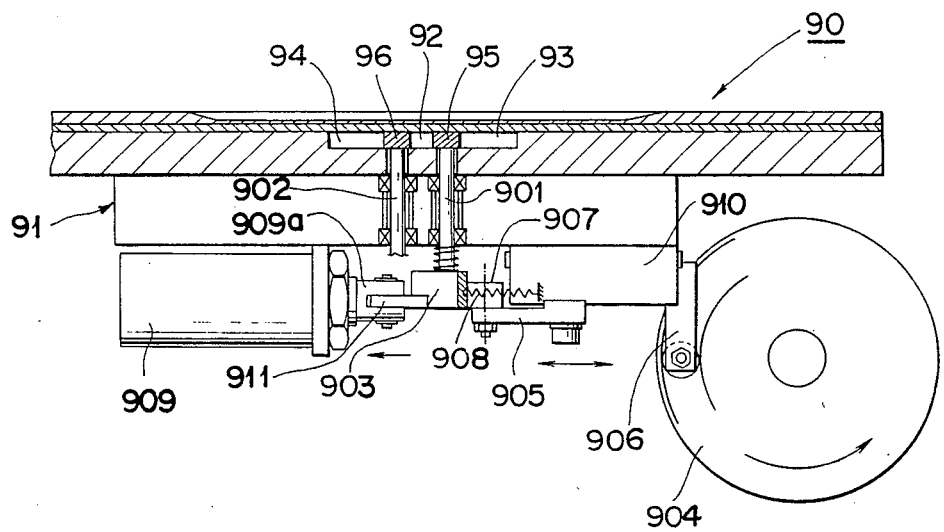
FIG. 14 is a schematic vertical sectional view of the chip sorting mechanism, taken on a plane indicated at FIG. 4 by a line B—B, wherein the sixth cover plate is arranged on the base of the chip sorting mechanism.

The chip sorting mechanism 90 serves as means to receive from the CPU 800 commands based on the check data of chips to sort the chips slipping down on the chip-passage body 42 into three groups, namely, acceptable chips, defective chips and unchecked chips. In the illustrated embodiment, where it is impossible, due to any trouble which may accidentally occur, to check certain chips, the chips are handled as unchecked chips. As shown in FIG. 4, the chip sorting mechanism 90 comprises a base 91 having first, second, third and fourth chip-passageways 91a, 92, 93 and 94 formed therein. The second chip-passageway 92 serves to discharge acceptable chips therethrough, the third chip-passageway 93 serves to discharge defective chips therethrough, and the fourth chip-passageway 94 serves to discharge unchecked chips therethrough. The base 91 is arranged on the inclined plane 101 of the apparatus body 100 in a manner that its first chip-passageway 91a is aligned with the groove 42a of the chip-passageway body 42, whereby the first chip-passageway 91a may receive chip-type components from the chip-passageway body 42. The second chip-passageway 92 extends linearly from the first chip-passageway 91a. The third and fourth chip-passageway 93 and 94 branch off to the right and left from the second passageway 92, respectively. At branch points of the third and fourth passageways 93 and 94, gate plates 95 and 96 are rotatably provided, respectively. The gate plates 95 and 96 serve as means to open and close the third and fourth chip-passageways 93 and 94, respectively, and serve as means to open and close the second passageway 92. On the base 91, a sixth cover plate (not shown) is arranged. Referring now to FIG. 14, shafts 901 and 902 are shown, which are rotatably supported by the base 91 and penetrate the base 91. The gate plate 95 is mounted on an upper end of the shaft 901 and the gate plate 96 is mounted on an upper end of the shaft 902. Mounted on a lower end of the shaft 901 is an arm 903. The chip sorting mechanism 90 further comprises a cam 904 rotatably supported by a support plate (not shown), a lever 905 connected at its one end to a slide bar (not shown) slidably fitted in a housing 910 which is provided on an undersurface of the base 91, and a solenoid 909 provided on the undersurface of the base 91. The unshown slide bar is connected at its one end to a cam follower 906 which is engaged with a cam surface of the cam 904. The lever 905 is provided at the other end thereof with a roller 907 which is forcedly contacted with the arm 903 of the shaft 902 by means of a spring 908 stretched between the arm 903 and the housing 910. Further, the arm 903 of the shaft 901 is connected through linkage means 911 to a solenoid pin 909a of the solenoid 909. Though unshown in FIG. 14, the shaft 902 has an arm provided on its lower end. Like the arm 903 of the shaft 901, the unshown arm of the shaft 902 is forcedly contacted with a roller of another lever (not shown), which is constructed in the same manner as the lever 905 and connected through another cam follower (not shown) to the cam 904, by means of a spring (not shown) stretched between the unshown arm of the shaft 902 and the housing 910. Further, the unshown arm of the shaft 902 is connected through linkage means (not shown) to a solenoid pin of another solenoid (not shown).

The manner of operation of the gate plates 95 and 96 will be described hereinafter with reference to FIGS. 15(a) to 15(c).

The gate plates 95 and 96 are adapted to be rotated and stopped by cooperation of the cam and the solenoids. More particularly, when the unshown solenoid for the gate plate 96 is not in operation and the cam 904 is rotated, the rotation of the cam 904 causes the roller of the unshown lever for the gate plate 96 to be forced toward the unshown arm of the shaft 902, whereby the arm and the shaft 902 are rotated while causing the unshown linkage means to be contracted, resulting in the gate plate 96 being rotated in a clockwise direction to open the fourth passageway 94 and close the second passageway 92 as shown in FIG. 15(a). At this time, the solenoid 909 for the gate plate 95 is in operation to cause the linkage means 911 to be extended, whereby the arm 903 is forced toward the roller 907 of the lever 905. Therefore, the rotation of the arm 903 which is to be caused by the cam 904 is prevented due to the force applied to the arm 903 by the actuation of the solenoid 909. Thus, the gate plate 95 is at a stopping position, namely, in a state of closing the third passageway 93 as shown in FIG. 15(a). In this state, unchecked chips from the first passageway 91a are directed toward the fourth passageway 94 by the gate plate 96, whereby the chips pass through the fourth passagway 94 to be discharged from the first passageway 94. In a state shown in FIG. 15(b), the solenoid 909 for the gate plate 95 and the unshown solenoid for the gate plate 96 are in operation. Therefore, the gate plates 95 and 96 are at stopping positions. In this state, acceptable chips from the first passageway 91a pass through the second passageway 92 to be discharged from the second passageway 92. In a state shown in FIG. 15(c), contrary to the state of FIG. 15(a), the gate plate 96 is at a stopping position because the unshown solenoid is in operation while the gate plate 95 is in a state of being rotated in a counterclockwise direction because the solenoid 909 is not in operation, namely, the gate plate 95 is in a state of opening the third passageway 93 and closing the second passageway 92. In this state, defective chips from the first passageway 91a are directed toward the third passageway 93 by means of the gate plate 95, whereby the chips pass through the third passageway 93 to be discharged from the third passageway 93. The solenoids are adapted to receive commands from the CPU 800 (FIG. 11) to be actuated or stopped. In the state shown in FIG. 15(a), when the non-shown solenoid for the gate plate 96 receives commands from the CPU 800 to be actuated, the actuation of the solenoid causes the unshown linkage means to be extended, whereby the unshown arm and the shaft 902 are rotated, resulting in the gate plate 96 being rotated in the counterclockwise direction. Then, the gate plate 96 comes into the state shown in FIG. 15(b). Also, in the state shown in FIG. 15(c), when the solenoid 909 receives commands from the CPU 800 to be actuated, the actuation of the solenoid 909 causes the linkage means 911 to be extended, whereby the arm 903 and the shaft 901 are rotated, resulting in the gate plate 95 being rotated in the clockwise direction. Then, the gate plate 95 comes into the state shown in FIG. 15(b).

Figure 15:
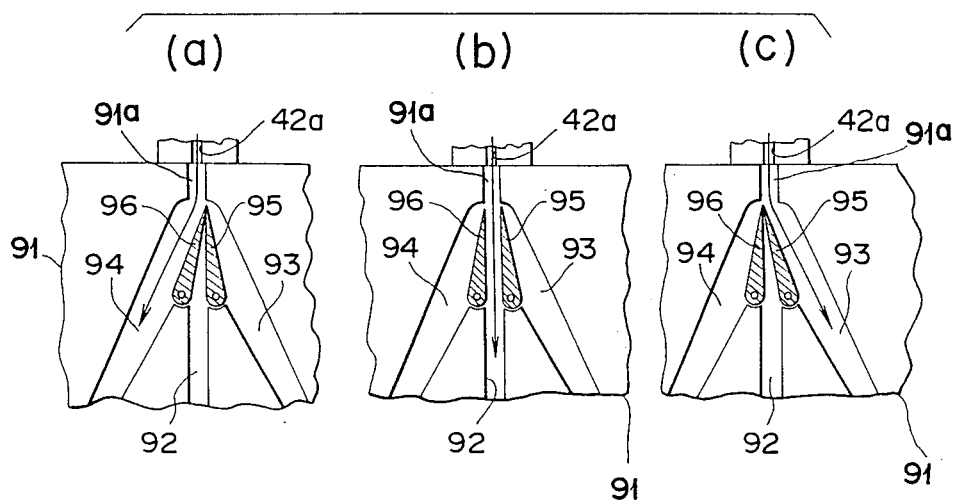
FIGS. 15(a) to 15(c) are each a schematic enlarged fragmentary plan view of assistance in explaining a manner of operation of gate plates of the chip sorting mechanism shown in FIG. 14, wherein the sixth cover plate is removed from the base of the chip sorting mechanism for clarity of illustration.

Incidentally, when the apparatus according to this invention is ordinarily stopped or stopped due to an urgent situation, the gate plate 96 is adapted to securely stop in the state of FIG. 15(a), whereby defective and unchecked chips are prevented from accidentally passing through the second passageway 92 for acceptable chips. Also, when commands indicative of defects of chips are continuously outputted some times (for example, five times), the apparatus is adapted to be stopped, whereby wrong checking of chips which may be brought about due to dirt, dust and/or the like being affixed to the chips can be prevented.

Figure 16A:
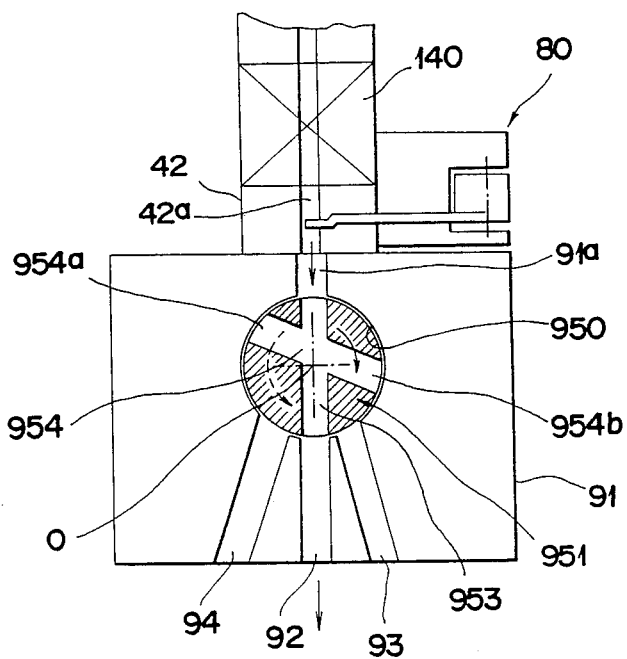
FIGS. 16(a) to 16(c) are each a schematic plan view showing a modification of the chip sorting mechanism shown in FIG. 14.
Figure 16B:
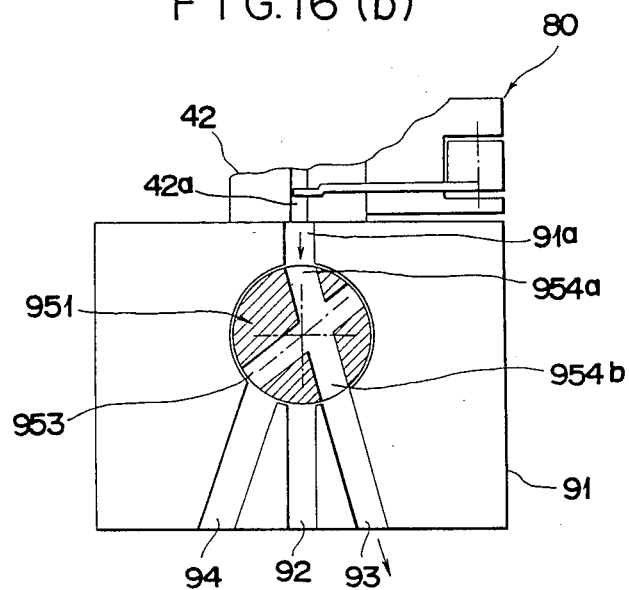
Figure 16C:
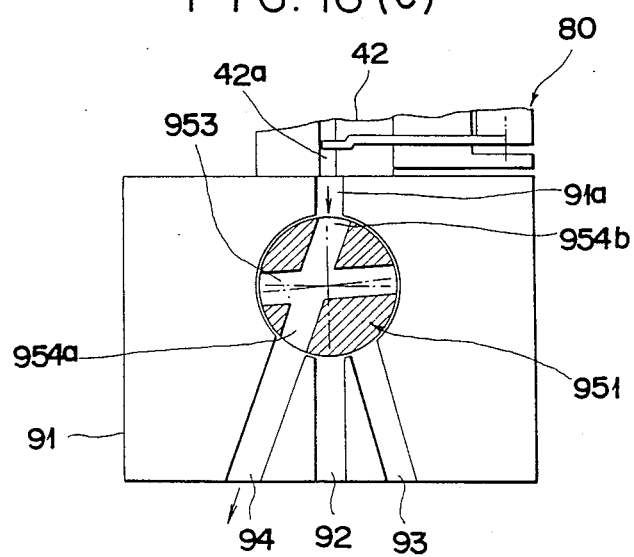

Referring now to FIGS. 16(a) through 16(c), there is illustrated a modification of the sorting mechanism 90 of FIG. 14. In the modification of FIGS. 16(a) through 16(c), parts which are identical to those shown in FIG. 14 are identified by the same designators and the description of them will not be repeated.

The base 91 of this modification has a large circular groove 950 formed in its area including the branch points of the chip-passageways 93 and 94. In the circular groove 950, a rotating disk 951 is received. The modification of FIGS. 16(a) through 16(c) comprises a motor (not shown) arranged below the base 91 and a motor control device (not shown) arranged below the base 91. A rotating shaft of the unshown motor penetrates the base 91 from a downward direction, on an upper end of which motor shaft the rotating disk 951 is mounted, whereby the rotating disk 951 is adapted to be rotated by the motor. The rotating disk 951 has a first linear groove 953 formed therein along a center line of the rotating disk 951 and a second linear groove 954 formed therein in such a manner that its axial line is slightly deviated from a center O of the rotating disk 951 and in a manner to transverse the first linear groove 953. The first linear groove 953 serves to direct acceptable chips from the first passageway 91a toward the second passageway 92 and the second linear groove 954 serves to direct defective and unchecked chips from the first passageway 91a toward the third and fourth passageways 93 and 94. When the first linear groove 953 of the rotating disk 951 is in communication with the first passageway 91a and the second passageway 92 as shown in FIG. 16(a), acceptable chips from the first passageway 91a pass through the first linear groove 953 of the rotating disk 951 to reach the second passageway 92 and are then discharged from the second passageway 92. Further, when the rotating disk 951 is rotated in a clockwise direction by means of the motor, one end portion 954a and the other end portion 954b of the second linear groove 954 of the rotating disk 951 become communicated with the first passageway 91a of the base 91 and the third passageway 93, respectively, as shown in FIG. 16(b), whereby defective chips from the chip-passage body 42 can pass through the first passageway 91 and the second linear groove 954 to reach the third passageway 93 and are then discharged from the third passageway 93. Furthermore, when the rotating disk 951 is rotated in a counterclockwise direction by means of the motor, the one end portion 954a and the other end portion 954b of the second linear groove 954 of the rotating disk 951 become communicated with the fourth passageway 94 of the base 91 and the first passageway 91a of the base 91, respectively, as shown in FIG. 16(c), whereby unchecked chips from the chip-passage body 42 can pass through the first passageway 91a and the second linear groove 954 of the rotating disk 951 to reach the fourth passageway 94 of the base 91 and are then discharged from the fourth passageway 94 of the base 91. It will be noted from the foregoing that, when the second passageway 92 of the base 91 is in communication with the first passageway 91a of the base 91 through the first linear groove 953 of the rotating disk 951, the third and fourth passageways 93 and 94 are closed by portions of the rotating disk 951; and when one of the third and fourth passageways 93 and 94 of the base 91 communicates with the first passageway 91a of the base 91 through the second linear groove 953, the other of the third and fourth passageways 93 and 94 of the base 91 and the second passageway 92 are closed by portions of the rotating disk 951. Incidentally, the rotation of the rotating disk 951 which allows the linear grooves 953 and 954 of the rotating disk 951 to communicate with the passageways 91a, 92, 93, and 94 of the base 91 is controlled by the unshown motor control device which is adapted to receive commands from the CPU 800 to be actuated. In the modification of FIGS. 16(a), through 16(c), the sorting operation of chips can be effected by only the rotating disk, the motor and the motor control device, so that the modification is simpler in structure than the chip sorting mechanism of FIG. 14.

Incidentally, when the apparatus according to this invention is ordinarily stopped or stopped due to an urgent situation, the rotating disk 951 is adapted to be stopped in the state of FIG. 16(c), whereby chips that are not yet sorted at this time are securely directed toward the fourth passageway 94. Also, when the state of the rotating disk 951 shown in FIG. 16(b) or 16(c) is continuously brought about, resulting in defective chips or unchecked chips passing through the second groove 954 of the rotating disk 951, the apparatus is stopped. At this time, the rotating disk 951 is adapted to stop in the state of FIG. 16(c).

As described above, in the method and apparatus for optionally checking the appearances of chips and sorting the chips, irradiating of straight and oblique light rays to a chip is carried out, so that each of the TV cameras may pick up a sharp image of the chip. Also, an image of a chip displayed on the screen of the monitor is swept at the selected addresses on the screen and processed in the CPU, so that it is possible to carry out the image processing at high speed. Further, chips are transferred on the chip-passage body in the predetermined direction by air jets, individually separated to be stopped at the checking positions, and automatically sorted on the basis of the check data obtained in the image processing sections, so that it is possible to speedily and precisely sort the chips. Furthermore, chips are transferred on the chip-passage body in the predetermined direction by air jets, so that even though a static electricity and/or a frictional resistance are produced between chips and the chip-passage body the chips can be smoothly transferred on the chip-passage body in the predetermined direction. Where the chip-passage body is inclined as described above, chips can slip down on the chip-passage body under the pull of gravity. In this case, the slipping-down of the chips on the chip-passage body is facilitated by air jet.

Preferably, the cover plates except the fourth cover plate will be constructed of transparent materials, e.g. tempered glass, to permit viewing the flow of chips in the groove of the chip-passage body. Also, both edges 42b(FIG. 10) of the U-shaped groove 42a of the chip-passage body are preferably sharpened in a manner that images of portions of the both edges 42b within view of the TV camera are not picked up due to the function of resolving power of the TV camera.

It will thus be seen that the objects set forth above, and those made apparent from the preceding description, are efficiently attained and, since certain changes may be made in the above construction without departing from the scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. A method of optically checking the appearances of chip-type components and sorting the chip-type components, comprising the steps of:
    a. feeding chip-type components onto chip-passage means to cause said chip-type components to run on said chip-passage means in a predetermined direction;
    b. during the running of said chip-type components on said chip-passage means, individually separating said chip-type components to stop said chip-type components one by one at each of two predetermined checking positions;
    c. irradiating light obliquely and straightly with respect to a chip-type component at one of said predetermined checking positions to pick up an optical image of one of undersurface and top surface sides of said chip-type component as a video signal by means of a first TV camera;
    d. irradiating light obliquely and straightly with respect to said chip-type component at the other of the predetermined checking positions to pick up an optical image of the other of the undersurface and top surface sides of said chip-type component as a video signal by means of a second TV camera;
    e. sending said video signals to image processing sections, each of which includes at least an analog-to-digital conversion unit, a video memory and a central processing unit, to process said video signals in said image processing sections and obtain data on the appearance of said chip-type component and a tilt angle of said chip-type component on each said predetermined checking position of said chip-passage means, and checking on the basis of said data whether said chip is acceptable or defective in its appearance; and
    f. thereafter sorting chip-type components on the basis of said check results.

2. A method of optically checking the appearances of chip-type components and sorting said chip-type components as defined in claim 1, wherein said step (a) further comprises the step of blowing air against said chip-passage means, whereby said chip-type components smoothly run on said chip-passage means.

3. A method of optically checking the appearances of chip-type components and sorting said chip-type components as defined in claim 1, wherein said chip-passage means consists of an elongate body having a substantially U-shape in a vertical section, whereby said chip-type components runs on said elongate body along a U-shaped groove of said elongate body.

4. A method of optically checking the appearances of chip-type components and sorting said chip-type components as defined in claim 3, wherein said step (a) further comprises the step of causing air to flow into said U-shaped groove of said elongate body, whereby said chip-type components smoothly run on said elongate body along said U-shaped groove of said elongate body.

5. A method of optically checking the appearances of chip-type components and sorting said chip-type components as defined in claim 1, wherein said chip-passage means is inclined at an angle of about 40°–50° with respect to the horizontal plane, whereby said chip-type components slip down on said chip-passage means.

6. A method of optically checking the appearances of chip-type components and sorting said chip-type components as defined in claim 3, wherein said elongate body is inclined at angle of about 40°–50° with respect to the horizontal plane, whereby said chip-type components slip down on said elongate body along said U-shaped groove of said elongate body.

7. A method of optically checking the appearances of chip-type components and sorting said chip-type components as defined in claim 5, wherein said step (a) further comprises the step of blowing air against said chip-passage means, whereby said chip-type components smoothly slip down on said chip-passage means.

8. A method of optically checking the appearances of chip-type components and sorting said chip-type components as defined in claim 6, wherein said step (a) further comprises the step of causing air to flow into said U-shaped groove of said elongate body, whereby said chip-type components smoothly slip down on said chip-passage means.

9. A method of optically checking the appearances of chip-type components and sorting said chip-type components as defined in claim 1, wherein said step (f) comprises the steps of classifying said chip-type components into three groups, acceptable, defective and unchecked.

10. A method of optically checking the appearances of chip-type components and sorting said chip-type components as defined in claim 1, wherein said step (f) is carried out by means of a sorting mechanism which comprises a base having a first passageway aligned with said chip-passage means and receiving said chip-type components from said chip-passage means therethrough, a second passageway extending as a continuation of said first passageway and receiving from said first passageway chip-type components appreciated as acceptable components in said step of checking said chip-type components to discharge said acceptable chip-type components therefrom, and third and fourth passageways branching off from said second passageway and receiving from said first passageway chip-type components appreciated as defective components in said checking step and chip-type components impossible to check in said checking step to discharge said defective and unchecked chip-type components therefrom, respectively; two gate members rotatably arranged at positions of said base which positionally correspond to branch points of said third and fourth passageways and adapted for closing and opening said second, third and fourth passageways; and actuating means for receiving commands from said image processing sections to actuate said gate members.

11. A method of optically checking the appearances of chip-type components and sorting said chip-type components as defined in claim 10, wherein said step (f) further comprises the steps of causing said sorting mechanism to be stopped when a predetermined number of defective and unchecked chip-type components are directed toward said third and fourth passageways by means of said gate members to continuously pass through said third and second passageways, respectively; and thereafter causing one of said gate members to be actuated so as to open said fourth passageway for unchecked chip-type components.

12. A method of optically checking the appearances of chip-type components and sorting said chip-type components as defined in claim 1, wherein said step (f) is carried out by means of a sorting mechanism which comprises a base having a first passageway aligned with said chip-passage means and receiving said chip-type components from said chip-passage means therethrough, a second passageway extending as a continuation of said first passageway and receiving from said first passageway chip-type components appreciated as acceptable components in said step of checking said chip-type components to discharge said acceptable chip-type components therefrom, and third and fourth passageways branching off from said second passageway and receiving from said first passageway chip-type components appreciated as defective components in said checking step and chip-type components impossible to check in said checking step to discharge said defective and unchecked chip-type components therefrom, respectively; two gate members rotatably arranged at positions of said base which positionally correspond to branch points of said third and fourth passageways and adapted for closing and opening said second, third and fourth passageways; and actuating means for receiving commands from said image processing sections to actuate said gate members; and wherein said step (f) further comprises the steps of causing said sorting mechanism to be stopped when a predetermined number of defective and unchecked chip-type components are directed toward said third and fourth passageways by means of said gate members to continuously pass through said third and second passageways, respectively; and thereafter causing one of said gate members to be actuated so as to open said fourth passageway for unchecked chip-type components.

13. A method of optically checking the appearances of chip-type components and sorting said chip-type components as defined in claim 1, wherein said individually separating of said chip-type components in said step (b) is carried out by means of a separating mechanism which comprises a first pin for stopping the foremost one of said chip-type components running on said chip-passage means; a second pin for holding the next chip-type component against said chip-passage means, said first and second pins being located above portions of said chip-passage means; and actuating means for causing said first and second pins to be moved upward and downward with respect to said chip-passage means.

14. A method of optically checking the appearances of chip-type components and sorting said chip-type components as defined in claim 1, further comprising the step of counting chip-type components running on said chip-passage means.

15. An apparatus for optically checking chip-type components and sorting said chip-type components, comprising:

a base;

chip-passage means mounted on said base and comprising an elongate body which has a substantially U-shape in a vertical section, said elongate body having two positions at which said chip-type components are to be checked and being formed at said two positions of transparent material;

a parts feeder mounted on said base, connected to one end of said elongate body of chip-passage means and feeding said chip-type components onto said elongate body of said chip-passage means;

a plurality of means for causing said chip-type components from said parts feeder to smoothly run along a U-shaped groove of said elongate body of said chip-passage means in a predetermined direction, and located at predetermined positions of said elongate body of said chip-passage means;

a separating mechanism for stopping said chip-type components from said parts feeder to separate said chip-type components one by one and arranged on said base so that it is located near a portion of said elongate body;

a first checking mechanism mounted on said base and optically checking, at one of said positions, one of undersurface and top surface sides of a chip-type component separated by means of said separating mechanism and comprising a first optical system and a first image processing section including at least an analog-to-digital conversion unit, a video memory and a central processing unit, said first optical system including at least first lighting means for straightly and obliquely irradiating light toward said chip-type component and a first TV camera for picking up, as a video signal, an image of said one of said sides of said chip-type component to which light rays from said first lighting means are obliquely and straightly irradiated, said first TV camera being electrically connected to said analog-to-digital conversion unit of said first image processing section;

a second checking mechanism mounted on said base so that it is located next to said first checking mechanism and adapted for optically checking, at the other of said positions, an image of the other of said undersurface and top surface sides of said chip-type component and comprising a second optical system and a second image processing section including at least an analog-to-digital conversion unit, a video memory and a central processing unit, said second optical system including at least second lighting means for straightly and obliquely irradiating light toward said chip-type component and a second TV camera for picking up, as a video signal, an image of the other side of said chip-type component to which light rays from said second lighting means are obliquely and straightly irradiated, said second TV camera being electrically connected to said analog-to-digital conversion unit of said second image processing section; and a sorting mechanism arranged at the other end of said elongate body of said chip-passage means and receiving said chip-type components from said elongate body to sort said chip-type components on the basis of check data obtained by said first and second checking mechanisms.

16. An apparatus for optically checking chip-type components and sorting said chip-type components as defined in claim 15, wherein said elongate body is inclined at angle of about 40°–50° with respect to the horizontal plane, whereby said chip-type components slip down on said elongate body along said U-shaped groove of said elongate body.

17. An apparatus for optically checking chip-type components and sorting said chip-type components as defined in claim 15, said means for causing said chip-type components to smoothly run along said U-shaped groove of said elongate body comprises air-passageways formed in said predetermined positions of said elongate body, and air-supplying means for causing air to flow into said U-shaped groove of said elongate body through said air-passageways.

18. An apparatus for optically checking chip-type components and sorting said chip-type components as defined in claim 15, further comprising cover plates which are arranged at said predetermined positions of said elongate body, and wherein said means for causing said chip-type components to smoothly run along said U-shaped groove of said elongate body comprises air-passageways formed in said cover plates and air-supplying means for causing air to flow into said U-shaped groove of said elongate body through said air-passageways.

19. An apparatus for optically checking chip-type components and sorting said chip-type components as defined in claim 15, further comprising a frosted glass plate which is arranged in a path of a central zone of light rays emitted from said lighting means of each of said first and second optical systems, thereby making contrast in brightness between a portion of a chip-type component illuminated by said central zone of the light rays and a portion of said chip-type component illuminated by a zone about said central zone of the light rays uniform.

20. An apparatus for optically checking chip-type components and sorting said chip-type components as defined in claim 15, wherein said separating mechanism comprises first and second pins which are located above said portion of said elongate body so as to be arranged at a predetermined interval therebetween along a longitudinal direction of said elongate body, and actuating means for receiving a command from said first and second image processing sections to cause said first and second pins to be moved vertically with respect to said elongate body.

21. An apparatus for optically checking chip-type components and sorting said chip-type components as defined in claim 15, wherein both edges of said U-shaped groove of said elongate body are sharpened, at each of said checking positions, such that images of portions of the both edges within a view of each of said first and second TV cameras are not picked up due to the function of resolving power of said TV camera.

22. An apparatus for optically checking chip-type components and sorting said chip-type components as defined in claim 15, further comprising a shutter device for stopping a chip-type component, which is separated by said separating mechanism, on each of said checking positions of said elongate body.

23. An apparatus for optically checking chip-type components and sorting said chip-type components as defined in claim 15, further comprising a counting mechanism adapted for counting said chip-type components running on said elongate body and mounted on said base so that it is located in advance of said sorting mechanism.

24. An apparatus for optically checking chip-type components and sorting said chip-type components as defined in claim 15, wherein said sorting mechanism comprises a base having first, second, third and fourth passageways formed therein, said first passageway receiving said chip-type components from said elongate body being and aligned with said U-shaped groove of said elongate body, said second passageway extending as a continuation of said first passageway and receiving from said first passageway chip-type components appreciated as acceptable components in said first and second checking mechanisms to discharge said acceptable chip-type components therefrom, and said third and fourth passageways branching off from said second passageway and receiving from said first passageway chip-type components appreciated as defective components in said first and second checking mechanisms and chip-type components impossible to check in said first and second checking mechanisms to discharge said defective and unchecked chip-type components therefrom, respectively;

two gate members rotatably arranged at positions of said base which positionally correspond to branch points of said third and fourth passageways and adapted for closing and opening said second, third and fourth passageways; and actuating means for receiving commands from said first and second image processing sections to actuate said gate members.

25. An apparatus for optically checking chip-type components and sorting said chip-type components as defined in claim 15, wherein said sorting mechanism comprises a base having a substantially circular recess, a first passageway communicating at its one end with said recess, and second, third and fourth passageways communicating with said recess, said first passageway communicating at the other end thereof with said U-shaped groove of said elongate body and receiving said chip-type components from said elongate body, said second passageway extending away from a portion of said recess, which is opposite to the forming position of said first passageway, so that it is aligned with said first passageway and adapted for receiving chip-type components appreciated as acceptable components in said first and second checking mechanisms to discharge said acceptable chip-type components therefrom, said third and fourth passageways extending away from portions of said recess so as to interpose said second passageway therebetween and receiving chip-type components appreciated as defective components in said first and second checking mechanisms and chip-type components impossible to check in said first and second checking mechanisms to discharge said defective and unchecked chip-type components therefrom respectively;

a circular rotating disk received in said recess of said base, said rotating disk having a first linear groove for allowing therethrough said first passageway and said second passageway to communicate with each other and formed along a center line of said rotating disk, and a second linear groove for allowing therethrough said first passageway and said third passageway to communicate with each other and for allowing therethrough said first passageway and said fourth passageway to communicate with each other, said second linear groove being formed in said rotating disk such that an axial line thereof is slightly deviated from a center of said rotating disk and so that said second linear groove traverses said first linear groove; and actuating means for receiving commands from said first and second image processing sections to cause said rotating disk to be rotated so that said first passageway and said second passageway are communicated with each other through said first linear groove of said rotating disk, said first passageway and said third passageway are communicated with each other through said second linear groove of said rotating disk, or said first passageway and said fourth passageway are communicated with each other through said second linear groove of said rotating disk.

26. An apparatus for optically checking chip-type components and sorting said chip-type components as defined in claim 25, wherein said actuating means comprises a motor arranged below said base of said sorting mechanism in such a manner that its rotating shaft penetrates said base of said sorting mechanism, said rotating disk mounted on said rotating shaft of said motor; and a motor control device for receiving commands from said first and second image processing sections to control the rotation of motor.

27. An apparatus for optically checking chip-type components and sorting said chip-type components as defined in claim 15, wherein each of said first and second optical systems comprises reflectors each adapted for reflecting a part of light rays which are emitted from said lighting means, obliquely with respect to a chip-type component on said chip-passage body.

28. An apparatus for optically checking chip-type components and sorting said chip-type components as defined in claim 15, wherein each of said first and second optical systems comprises a first light irradiating head connected through a first fiber cable to said lighting means and obliquely irradiating light from said lighting means with respect to a chip-type component on said chip-passage body; and a second light irradiating head connected through a second fiber cable to said lighting means and straightly irradiating light from said lighting means with respect to said chip-type component on said chip-passage body.

* * * * *